United States Patent [19]

Packard

[11] Patent Number: 5,698,067
[45] Date of Patent: Dec. 16, 1997

[54] PROTECTOR FOR A ROLL OF TAPE

[75] Inventor: Joy A. Packard, Somerset, Wis.

[73] Assignee: MinnesotaMining and Manufacturing Company, St. Paul, Minn.

[21] Appl. No.: 582,161

[22] Filed: Jan. 2, 1996

[51] Int. Cl.$^6$ .................................................. B32B 31/00
[52] U.S. Cl. .................... 156/577; 156/579; 242/588.3
[58] Field of Search ..................... D19/65, 67, 69, D19/89; 156/577, 579; 242/588.3, 588.6; 225/5, 6, 7, 15, 19, 24, 25, 46, 56

[56] References Cited

U.S. PATENT DOCUMENTS

| | | | |
|---|---|---|---|
| D. 125,085 | 2/1941 | Jackson. | |
| D. 141,220 | 5/1945 | Preble, Jr.. | |
| D. 164,733 | 10/1951 | Pretzfelder, Jr.. | |
| D. 185,284 | 5/1959 | Hofmann | D74/1 |
| D. 295,424 | 4/1988 | Porter | D19/67 |
| 1,869,729 | 8/1932 | Zuckerman | 225/7 X |
| 2,275,212 | 3/1942 | Valentine. | |
| 2,295,477 | 9/1942 | Jackson. | |
| 2,295,679 | 9/1942 | Montbach | 242/55.5 |
| 2,790,609 | 4/1957 | Hawthorne et al. | 242/55.5 |
| 4,060,444 | 11/1977 | Schweig, Jr. et al. | 156/391 |
| 5,154,335 | 10/1992 | Bredow et al. | 225/40 |

OTHER PUBLICATIONS

"3M Surgical Tape Sampler, Standards that never vary", brochure, 3M Health Care, 1993.

"3M Micropore™ Surgical Tape, The dependable choice for a gentle, general dressing paper tape.", 2 page brochure, 3M Health Care, 1995.

Engineering Drawings for the Micropore™ Surgical Tape Dispenser illustrated on the back of the 2 page brochure, which dispenser was sold more than one year prior to the filing date of the present application (3 pages).

2 Photographs of a prior art edge protector for use with Smith & Nephew medical tape rolls, which edge protector does not afford rotation of the roll of tape relative to edge protector.

*Primary Examiner*—James Engel
*Attorney, Agent, or Firm*—Gary L. Griswold; Walter N. Kirn; Jeffrey J. Hohenshell

[57] ABSTRACT

A two-piece edge protector for a roll of tape is described. The protector has a pair of sides and transverse, peripheral tape anchors which may receive a leading portion of a roll of tape to assist in dispensing the tape. The protector is particularly suitable to protect a roll of hand tearable medical tape.

19 Claims, 5 Drawing Sheets

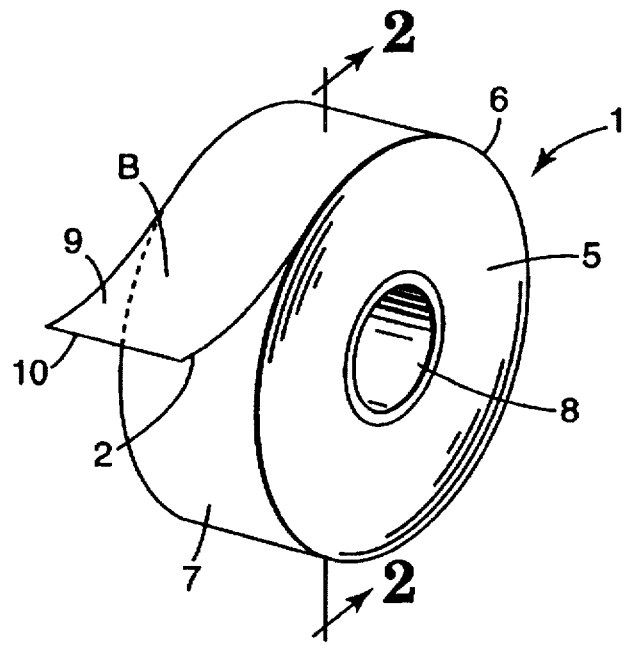
Fig. 1
PRIOR ART
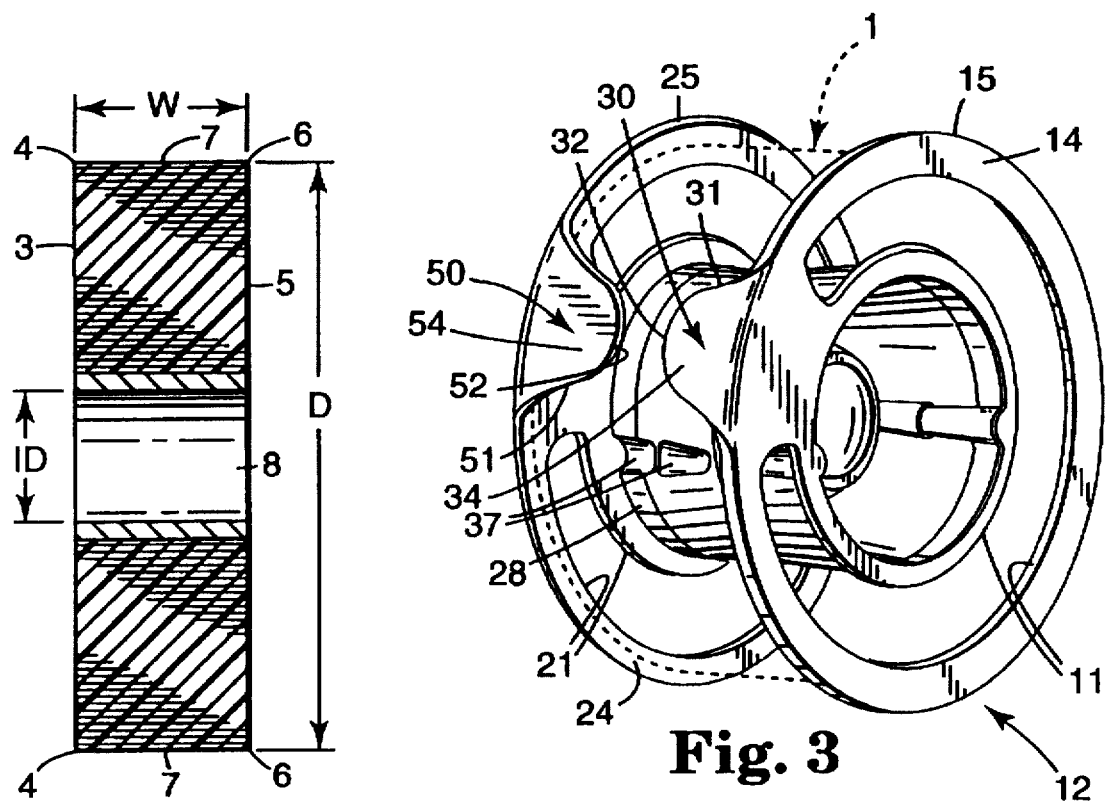
Fig. 2
PRIOR ART
Fig. 3

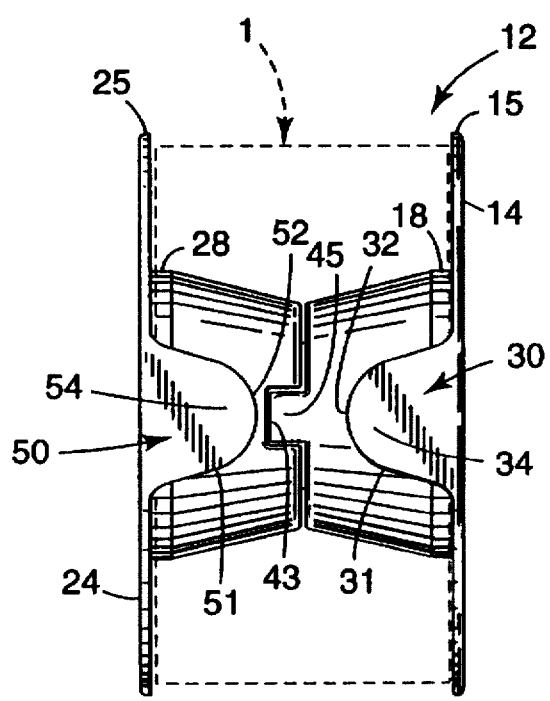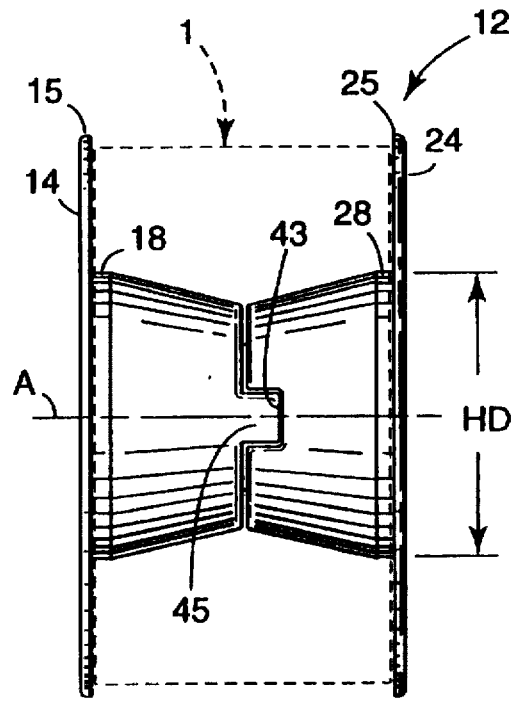
Fig. 4
Fig. 5
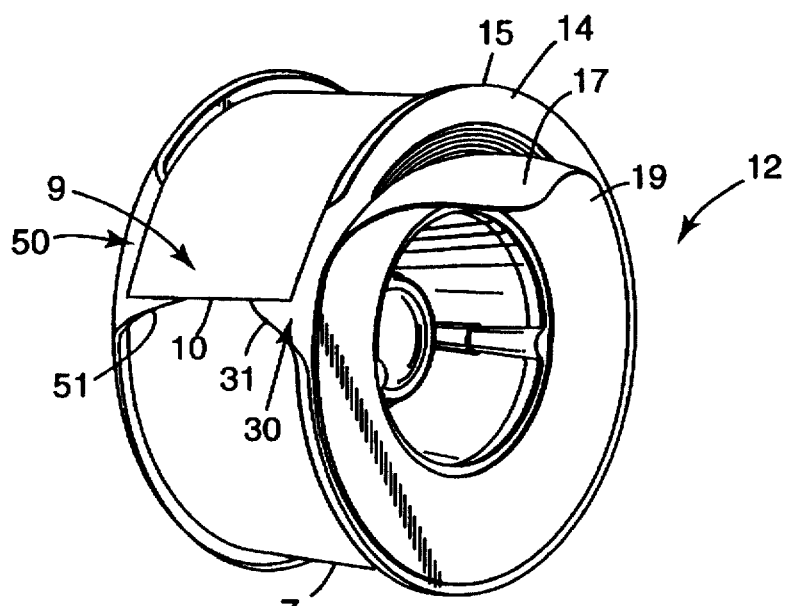
Fig. 9

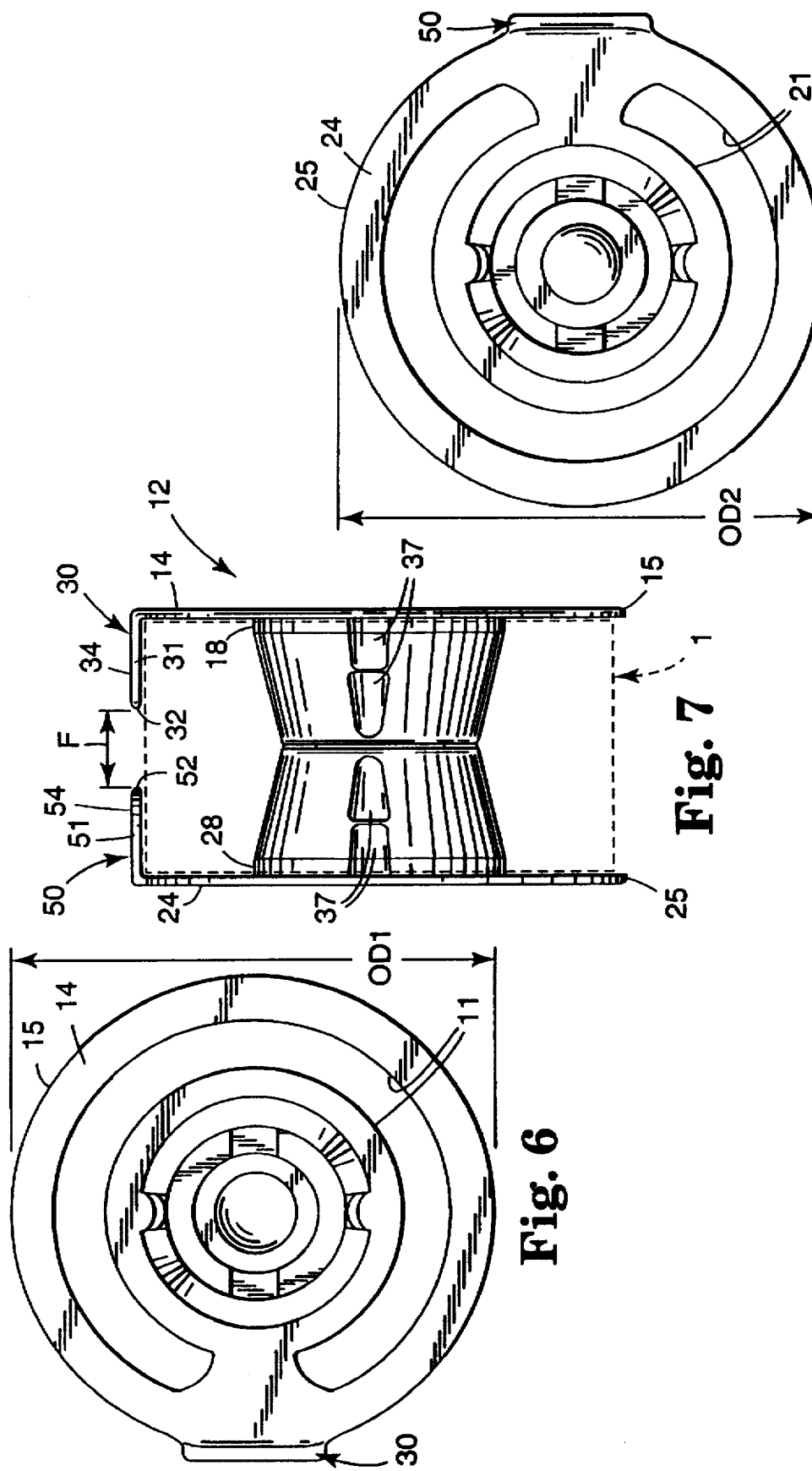

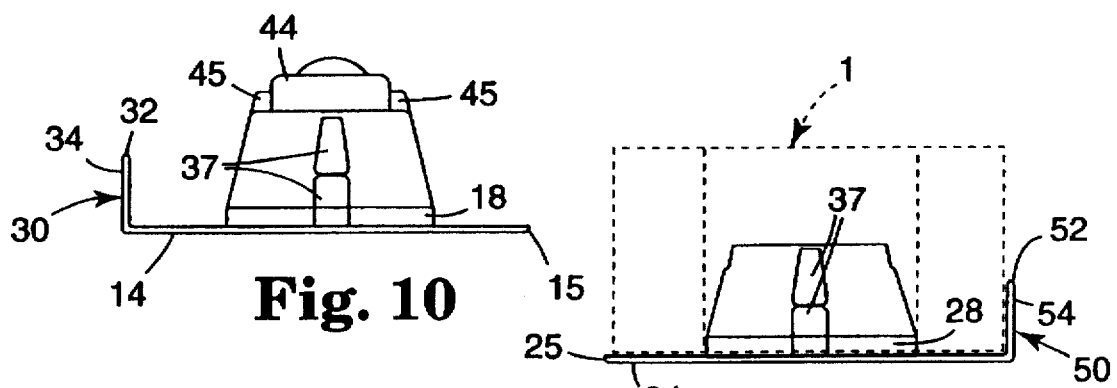
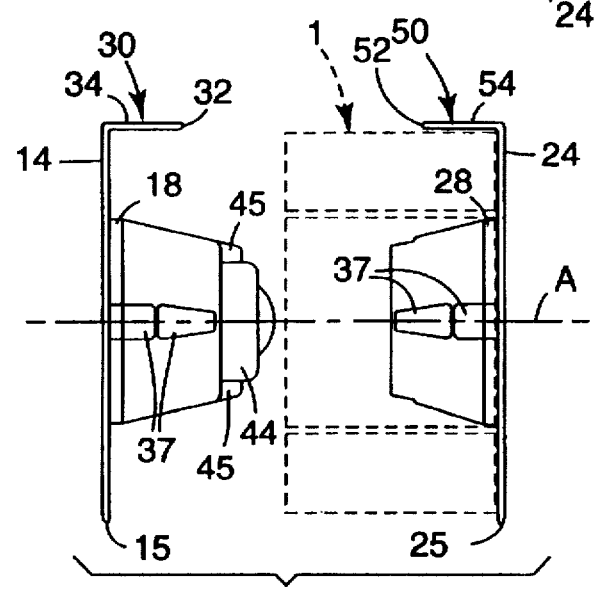
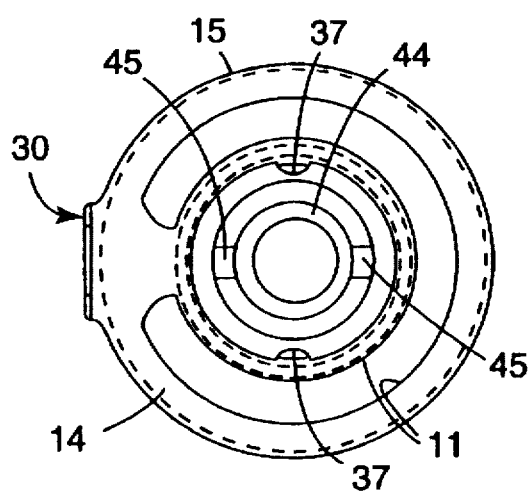
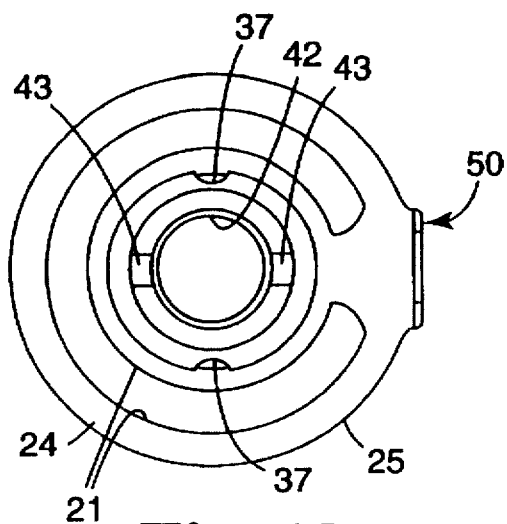

PROTECTOR FOR A ROLL OF TAPE

TECHNICAL FIELD

The present invention is directed to a protector for a roll of tape, and more particularly to a two-piece protector for a roll of manually tearable medical tape.

BACKGROUND

FIGS. 1 and 2 illustrate a typical, prior art roll of tape 1. The tape roll 1 typically has a length of tape wound about a core 8. The core 8 has an inner diameter ID. The length of tape includes a backing B with a pressure-sensitive adhesive 2 coated on at least portions of at least one side of the backing B. When in roll form, the tape has a leading end portion 9. The tape roll 1 includes a pair of sides 3 and 5, a pair of edges 4 and 6, a width W and an outer peripheral surface 7 defining an outer diameter D.

The art is replete with different types of tape rolls designed for a multitude of uses. One type of tape is known in the art as medical tape. As used herein, the phrase "medical tape" means a tape which is designed for use in the health care field. Examples of medical tapes include a) Transpore™ Surgical Tape which is a transparent, easy-to-tear, perforated plastic tape for securing dressings or devices, b) Micropore™ Surgical Tape which is a gentle, general purpose paper tape, c) Durapore™ Surgical Tape which is a cloth tape with strong adhesion for securing dressings or devices, d) Microfoam™ Surgical Tape which is a highly conformable elastic foam tape for compression applications or securing dressings on difficult or challenging areas, and e) Blenderm™ Surgical Tape which is an occlusive, transparent plastic tape that protects wounds from fluids and contaminants. Each of these particular examples of medical tapes is available from Minnesota Mining and Manufacturing Co. (3M) of St. Paul, Minn.

A number of problems are associated with the use of a roll of tape. Many persons may find it difficult or inconvenient to locate the leading end portion 9 of the tape. Often the leading end portion 9 is adhered to the rest of the tape roll 1 making the leading end 10 difficult to find.

Adhesive along the sides 3 and 5 of the roll of tape tends to accumulate dust, dirt and other contaminants. This is particularly a problem for rolls of medical tape which should be kept as clean as possible. The leading end portion 9 of the tape is often wasted when a user elects to simply dispose of the exposed leading end portion 9 in favor of a more pristine portion of the tape. Exposed adhesive along the leading end portion 9 and adhesive along the sides 3 and 5 of the tape tend to stick to clothing or other surfaces which may contaminate the surface and make use of a tape roll 1 inconvenient.

Another problem associated with the use of a roll of tape is that some tape rolls may become easily damaged or altered. It is generally desirable to protect the tape roll (particularly the edges) from scuffs, mars, indentations or other deformations as such deformations may adversely affect the performance of the tape.

Dispensers have been developed over the years to address the problems associated with the use of tape rolls. Many of these dispensers are complex, relatively expensive devices that can be difficult to manufacture.

The art is replete with tape roll dispensers or other devices which include serrations, teeth, blades, tearing edges or other cutting means designed to help separate a leading end portion of a roll of tape from the remaining tape on the roll. Examples of such devices are disclosed in U.S. Pat. Nos. 2,295,679 (Montbach), 2,295,477 (Jackson), 2,790,609 (Hawthorne), 4,060,444 (Schweig, Jr. et al.), Des. 141,220 (Preble), Des. 164,733 (Pretzfelder), Des. 125,085 (Jackson), and Des. 185,284 (Hofmann). Another example of a dispenser with a cutting means comprises the dispenser for use with Micropore™ Surgical Tape. That dispenser has been on sale more than one year prior to the filing date of the present application.

For a roll of manual or hand tearable tape, a cutting means may be unnecessary. A dispenser with a cutting means may also be undesirable in some situations. Cutting means have the potential to scratch or otherwise damage surfaces (e.g. clothing). Cutting means may also cause the dispenser to snag on surfaces which may reduce the convenience for the user. Generally, cutting means also add cost to the dispenser and complicate the manufacturing process.

The prior art also includes an edge protector for use with a roll of medical tape sold by Smith and Nephew. That edge protector comprises two separate pieces which are releasably attached to respective sides of the core 8 of the tape roll. The edge protector does not allow the roll of tape 1 to rotate relative to the edge protector which may adversely affect the ease with which the tape may be dispensed for some users. The prior art edge protector also lacks any surface radially above the outer peripheral surface of the tape which may be utilized to receive a leading end portion of the tape.

BRIEF DESCRIPTION OF THE INVENTION

In one aspect, the present invention comprises a protector for a roll of tape. The roll of tape has a leading end portion of tape, a pair of sides and edges, a width, an outer peripheral surface defining an outer diameter, and a core defining an inner diameter. While the protector is particularly suitable for a roll of hand tearable, medical tape, the protector may also be utilized with other types of tapes.

The protector comprises a first side element comprising a first side wall having an outer periphery, and a first hub portion; a second side element comprising a second side wall having an outer periphery, and a second hub portion. The protector has a releasable hub means for releasably attaching the first hub portion to the second hub portion to form a hub adapted to receive the roll of tape. The resulting hub has an axis and an outer hub diameter that is sized and shaped to afford free rotation of the roll of tape about the hub. The hub is adapted to receive the roll of tape in one of either a) a first orientation which affords clockwise rotation of the roll of tape about the axis of the hub, or b) a second orientation which affords counterclockwise rotation of the roll of tape about the axis of the hub. Preferably, the outer hub diameter is less than the inner diameter of the core of the roll of tape to afford free rotation of the roll of tape about the hub.

More preferably, the releasable hub means comprises one of the first and second hub portions having a socket portion and the other of the first and second hub portions having a protruding portion adapted to be received in the socket portion in an interference or snap fit. Also preferably, the protector includes stabilizing means for restricting rotation of the first side element relative to the second side element. For example, the stabilizing means may comprise one of the first and second hub portions having a key and the other of the first and second hub portions having a slot adapted to receive the key when the releasable hub means forms the hub. The key and slot are situated to resist rotation of the first side element relative to the second side element.

The first side element has a first transverse, peripheral tape anchor projecting axially away from the first side wall and toward the second side wall. The first tape anchor has an axially innermost point and a land surface adapted to have a portion of the leading end portion of the tape adhered thereto when the roll of tape is mounted in either the first or the second orientation. The second side element has a second transverse, peripheral tape anchor projecting axially away from the second side wall and toward the first side wall. The second tape anchor has an axially innermost point and a land surface adapted to have a portion of the leading end portion of the tape adhered thereto when the roll of tape is mounted in either the first or the second orientation.

The axially innermost points of the first and second tape anchors define a finger channel therebetween which affords passage of a user's digit to afford removal of the leading end portion of the tape from the land surfaces of the first and second tape anchors. Preferably the minimum distance between the axially innermost points of the first and second tape anchors is approximately ⅜ inches.

The outer peripheries of the first and second side walls are free of any portions extending therebetween other than the peripheral bridge portion to provide an opening for access to the outer peripheral surface of the roll of tape. This feature adds a degree of convenience to the protector to help a user dispense a preselected length of tape from the roll as it affords easier access to the leading end portion of the tape. Preferably, the protector is free of any teeth or serrations for cutting the tape with the attendant disadvantages associated with such teeth or serrations.

The protector is constructed from an inexpensive plastic material selected from the group consisting of polystyrene, polyethylene, polypropylene and polycarbonate. Preferably, the protector comprises two pieces which may be assembled to provide the protector of the present invention.

In another aspect, the present invention comprises a method of protecting a roll of tape having a leading end portion of tape, a pair of sides and edges, a width, an outer peripheral surface defining an outer diameter, and a core defining an inner diameter. The method comprises the steps of: A) providing a protector comprising: i) a first side element comprising a first side wall having an outer periphery, and a first hub portion; a second side element comprising a second side wall having an outer periphery, and a second hub portion; ii) releasable hub means on the first and second side elements for releasably attaching the first hub portion to the second hub portion to form a hub adapted to receive the roll of tape, the hub having an axis and an outer hub diameter that is sized and shaped to afford free rotation of the roll of tape about the hub, the hub being adapted to receive the roll of tape in one of either a) a first orientation which affords clockwise rotation of the roll of tape about the axis of the hub, or b) a second orientation which affords counterclockwise rotation of the roll of tape about the axis of the hub, iii) the first side element having a first transverse, peripheral tape anchor projecting axially away from the first side wall and toward the second side wall, the first tape anchor having an axially innermost point and a land surface adapted to have a portion of the leading end portion of the tape adhered thereto when the roll of tape is mounted in either the first or the second orientation, the second side element having a second transverse, peripheral tape anchor projecting axially away from the second side wall and toward the first side wall, the second tape anchor having an axially innermost point and a land surface adapted to have a portion of the leading end portion of the tape adhered thereto when the roll of tape is mounted in either the first or the second orientation, the axially innermost points of the first and second tape anchors defining a finger channel therebetween which affords passage of a user's digit to afford removal of the leading end portion of the tape from the land surfaces of the first and second tape anchors, iv) wherein the outer peripheries of the first and second side walls are free of any portions extending therebetween other than the first and second tape anchors to provide an opening for access to the outer peripheral surface of the roll of tape; B) placing the second side wall substantially opposite the first side wall, C) placing the roll of tape between the first and second hub portions; and D) forming a hub which receives the roll of tape by releasably attaching the first hub portion to the second hub portion.

BRIEF DESCRIPTION OF THE DRAWINGS

The present invention will be further described with reference to the accompanying drawing wherein like reference numerals refer to like parts in the several views, and wherein:

FIG. 1 is a perspective view of a prior art roll of tape;

FIG. 2 is a sectional view of the roll of tape of FIG. 1, taken approximately along lines 2—2 of FIG. 1;

FIG. 3 is a perspective view of a protector for a roll of tape according to the present invention with dashed lines generally illustrating the position of an unused roll of tape when placed in the protector;

FIG. 4 is a front view of the protector of FIG. 3 which illustrates the position of the roll of tape with dashed lines;

FIG. 5 is a rear view of the protector of FIG. 3 which illustrates the position of the roll of tape with dashed lines;

FIG. 6 is a right side view of the protector of FIG. 3;

FIG. 7 is a bottom view of the protector of FIG. 3 with dashed lines illustrating the portion of the roll of tape mounted on a hub in the protector which is formed by first and second hub portions attached together;

FIG. 8 is a left side view of the protector of FIG. 3;

FIG. 9 is a perspective view of the protector according to the present invention with a roll of tape mounted therein and showing a label which is affixed to the side of the protector and the label partially peeled away;

FIG. 10 is a top view a one of the two pieces which may be assembled to provide the protector according to the present invention;

FIG. 11 is a top view of a piece which may be assembled with the piece of FIG. 10 to provide the protector according to the present invention, with a roll of tape illustrated with dashed lines;

FIG. 12 is a side view of the piece of FIG. 10;

FIG. 13 is a side view of the piece of FIG. 11;

FIG. 14 illustrating the pieces of FIGS. 10 and 11 being assembled to provide the protector according to the present invention with a roll of tape shown with dashed lines.

DESCRIPTION OF THE PREFERRED EMBODIMENT

Figure 15:
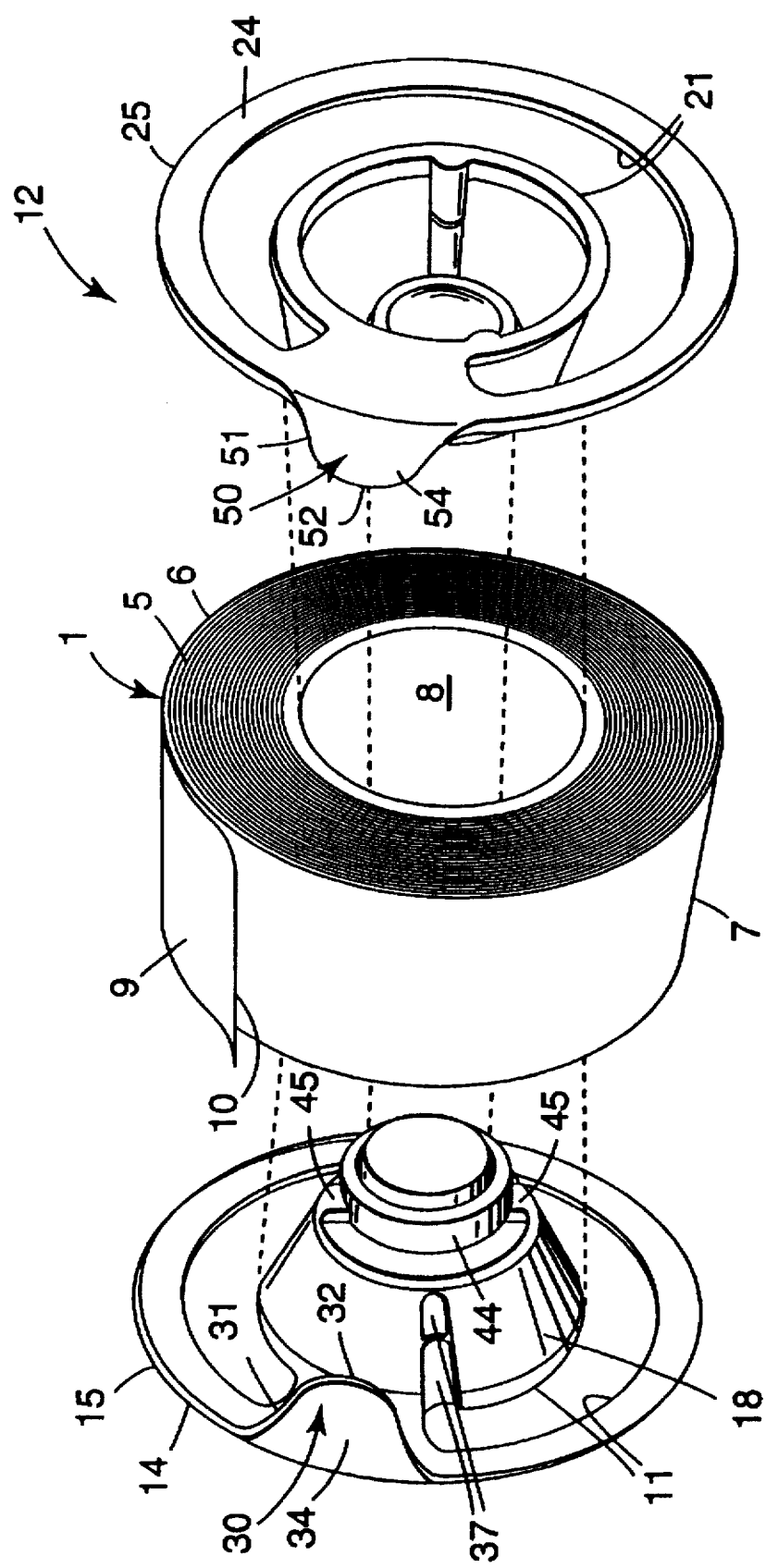
FIG. 15 is a perspective view of the protector according to the present invention with a roll of tape.

Referring now to FIGS. 3 through 15 of the drawing there is shown a protector according to the present invention generally designated by reference character 12. While the protector 12 is suitable for protecting or dispensing almost any type or style of tape roll 1, the protector 12 is particularly suitable for protecting and dispensing a roll of manually tearable, medical tape. Examples of such manually tearable medical tape include: a) Transpore™ Surgical Tape, b) Micropore™ Surgical Tape, c) Durapore™ Surgical Tape, d) Microfoam™ Surgical Tape, and e) Blenderm™ Surgical Tape; each of which is available from Minnesota Mining and Manufacturing Co. (3M) of St. Paul, Minn. As used herein, the phrases "hand tearable tape" or "manually tearable tape" mean a tape that may be separated or torn apart by a person of ordinary strength and coordination. A variety of factors may render a tape manually or hand tearable. For example, the tape backing may be constructed from a readily tearable material such as paper, cloth or a nonwoven material such as rayon. Perforations, edge geometries, or other alterations of the tape backing B may also render tape manually or hand tearable.

The protector 12 comprises a first side element having a first side wall 14 with an outer periphery 15. Preferably, the first side wall 14 has surfaces defining a cut-out or hole 11 to reduce the mount of material required to make the first side wall 14 with the attendant cost advantage. As best seen in FIG. 9, a label 19 may be adhesively adhered to the first side wall 14 by adhesive 17 to cover the hole 11. The label may optionally include information printed thereon, such as the type of protector 12 or the type of tape roll 1. The outer periphery 15 has a substantially circular portion defining an outer diameter OD1. More preferably, the outer diameter OD1 is at least as large as the outer diameter D of the roll of tape 1 so that the first side wall 14 and the label 19 may completely cover the roll of tape 1, as opposed to some prior art tape dispensers which leave a portion of the roll of tape (e.g. portions of its side or edge) exposed to potential damage or contamination. An example of such a prior art dispenser is shown in U.S. Pat. No. 4,060,444. Alternatively, the hole 11 may be eliminated. The first side element also has a first hub portion 18.

The protector 12 also has a second side element that is independent of and separate from the first side element. The second side element comprises a second side wall 24 adapted to be placed substantially opposite the first side wall 14 (as shown in FIG. 3). The second side wall 24 has an outer periphery 25. Preferably, the second side wall has a hole 21 similar to hole 11 and a label 19. The outer periphery 25 also preferably has a substantially circular portion defining an outer diameter OD2 which is at least as large as the outer diameter D of the roll of tape 1 so that the second side wall 14 and the label 19 completely cover the roll of tape 1, as opposed to the prior art tape dispensers mentioned above. As best seen in FIG. 15, the outer periphery 15 of the first side wall 14 is preferably substantially the same shape as the outer periphery 25 of the second side wall 24. Also preferably, the diameter OD1 of the first side wall is approximately equal to the diameter OD2 of the second side wall. As an example not intended to be limiting, the diameters OD1 and OD2 may be approximately 2 and 5/16 inches.

The second side element also has a second hub portion 28. The protector 12 includes a releasable hub means for releasably attaching the first hub portion 18 to the second hub portion 28 to form a hub adapted to receive the roll of tape 1. The hub has an axis A and an outer hub diameter HD (FIG. 5). Preferably, the outer hub diameter HD is sized and shaped to afford free rotation of the roll of tape 1 about the hub. In particular, the outer hub diameter HD is less than the inner diameter ID of the core 8 of the roll of tape to afford free rotation of the roll of tape 1 about the hub. Optionally, but not preferably, the outer hub diameter HD may be approximately equal to the inner diameter ID of the core 8 of the roll of tape to fixedly attach the protector 12 relative to the roll of tape.

The hub is adapted to receive the roll of tape in one of either a) a first orientation (e.g. one of FIGS. 9 or 15) which affords clockwise rotation of the roll of tape 1 about the axis of the hub, or b) a second orientation (the other of FIGS. 9 or 15) which affords counterclockwise rotation of the roll of tape about the axis A of the hub. The protector 12 is preferably universal in that the protector 12 functions the same regardless of whether the roll of tape 1 is in the first or the second orientation.

The first side element has a first transverse, peripheral tape anchor 30 that projects axially away from the first side wall 14 and toward the second side wall 24 when the protector 12 is in an assembled condition. The first tape anchor 30 has an axially innermost point 32 and a land surface 34 adapted to have a portion of the leading end portion 9 of the tape adhered thereto when the roll of tape 1 is mounted in either the first or the second orientation (see FIGS. 9 and 15). Preferably, the first tape anchor 30 has an arcuate edge surface 31.

The second side element has a second transverse, peripheral tape anchor 50 that projects axially away from the second side wall 24 and toward the first side wall 14. The second tape anchor 50 has an axially innermost point 52 and a land surface 54 adapted to have a portion of the leading end portion 9 of the tape adhered thereto when the roll of tape is mounted in either the first or the second orientation. Preferably, the second tape anchor 50 has an arcuate edge surface 51. The edges 31 and 51 are preferably identical to contribute to the universal feature of the protector 12. The universal feature of the protector 12 adds a degree of convenience to the function and assembly of the protector 12 as a user need not be concerned with the orientation of the tape when it is mounted on the hub.

The axially innermost points 32 and 52 define a finger channel F (FIG. 7) therebetween which affords passage of at least a portion of a user's digit to afford removal of the leading end portion of the tape from the land surfaces 34 and 54. The tape anchoring surfaces 34 and 54 are situated in a position that is spaced from the outer peripheral surface 7 of the roll of tape to aid the user in identifying the location of the leading end 10 of the tape.

In order to enhance the user's access to the outer peripheral portion 7 of the roll of tape 1, the outer peripheries 15 and 25 of the first and second side walls are free of any portions extending therebetween other than the anchors 30 and 50 to provide an opening. A user may place his or her finger in the opening and between the first and second walls 14 and 24 to obtain easy access to the outer peripheral surface 7 of the roll of tape.

The edges 31 and 51 are sized and shaped to engage a user's digit to assist in removing the leading end portion 9 of the tape from the land surfaces 34 and 54. As an example not intended to be limiting, the distance between the walls 14 and 24 may be about one and one-eighth inches and the width of the finger channel or opening F may be about 3/8 inches.

If leading end portion 9 of the tape 1 is adhered to one or more of land surfaces 34 and 54, a user may place his or her finger through the opening between the outer peripheries 15 and 25 and run it along the outer peripheral portion of the tape 7 until it engages the leading end 10 of the tape and either or both of the edges 31 and 51 (e.g. the side of the edge 31 or 51 which is closest to the leading end 10 of the tape). The structure of the protector 12 allows the user to easily grasp the leading portion 9 of the tape and unwind a preselected portion of the tape from the roll 1. Once the preselected portion of the tape is unwound, the preselected portion of tape may be separated from the roll 1. To separate the preselected portion of tape, a user may adhere a portion of the tape to one or more of the land surfaces 34 or 54 to assist the user in separating the preselected portion of tape from the rest of the roll 1. In this manner, the protector 12 assists the user in creating a tearing force to separate the preselected portion of tape. This operation may be repeated until all of the tape is used, at which time the roll of tape may be replaced and the protector 12 reused.

Also preferably, the protector 12 is free of any teeth, cutting surfaces, blades, tearing edges, or serrations for cutting the tape. Such a cutting means may be unnecessary if the roll of tape comprises a manually tearable tape, or if the user prefers to use a separate, independent cutting means such as a pair of scissors. As a result of the lack of a cutting means, the protector 12 may be conveniently handled without concern for the protector 12 scratching or otherwise damaging a surface. The protector 12 can be readily stored in and removed from the pocket of a user's clothing without concern for damage to the clothing. Additionally, the lack of a cutting means provides a dispenser which is relatively inexpensive, and free of complex cutting surfaces which may require careful monitoring during manufacture.

The protector 12 is constructed from an inexpensive, plastic material. The protector 12 is preferably, constructed from a plastic material selected from the group consisting of polystyrene, polyethylene, polypropylene and polycarbonate. Preferably, the protector comprises two parts. Any suitable construction technique may be utilized to create the parts for the protector 12, including, but not limited to vacuum forming, pressure forming or injection molding. As an example not intended to be limiting, the parts for the protector 12 may be constructed from thermoformed, high impact polystyrene (0.03 inch THK DOW #484, with 15%–20% regrind).

The releasable hub means preferably comprises one of the first and second hub portions 18 and 28 having a socket portion 42 (FIG. 13) and the other of the first and second hub portions having a protruding portion 44 (FIG. 12) adapted to be received in the socket portion 42 (FIG. 13) in an interference or snap-fit. Optionally, the protruding portion 44 (FIG. 12) and socket 42 (FIG. 13) may have reverse tapers which, in cooperation with an interference fit, serve to bias the hub portions toward a locked or closed position.

The protector 12 further includes stabilizing means for restricting rotation of the first side element relative to the second side element. Preferably, the stabilizing means comprises one of the first and second hub portions having a key 45 and the other of the first and second hub portions having surfaces defining a slot 43 adapted to accept the key 45 when the releasable hub means forms the hub. The key 45 and slot 43 are situated to resist rotation of the first side element relative to the second side element. Optionally, strengthening indents 37 may be present on the hub to add strength to the protector 12.

METHOD

The present invention also may be viewed as a method of protecting a roll of tape 1. The method comprises the step of: A) providing a protector 12 comprising: i) a first side element including a first side wall 14 having an outer periphery 15, and a first hub portion 18; a second side element comprising a second side wall 24 having an outer periphery 25, and a second hub portion 28; ii) releasable hub means for releasably attaching the first hub portion 18 to the second hub portion 28 to form a hub adapted to receive the roll of tape, the hub having an axis and an outer hub diameter that is sized and shaped to afford free rotation of the roll of tape 1 about the hub, the hub being adapted to receive the roll of tape 1 in one of either a) a first orientation which affords clockwise rotation of the roll of tape 1 about the axis of the hub, or b) a second orientation which affords counterclockwise rotation of the roll of tape 1 about the axis of the hub, iii) the first side element having a first transverse, peripheral tape anchor 30 projecting axially away from the first side wall 14 and toward the second side wall 24, the first tape anchor 30 having an axially innermost point 32 and a land surface 34 adapted to have a portion of the leading end portion 9 of the tape adhered thereto when the roll of tape 1 is mounted in either the first or the second orientation, the second side element having a second transverse, peripheral tape anchor 50 projecting axially away from the second side wall 24 and toward the first side wall 14, the second tape anchor 50 having an axially innermost point 52 and a land surface 54 adapted to have a portion of the leading end portion 9 of the tape adhered thereto when the roll of tape is mounted in either the first or the second orientation, the axially innermost points 32 and 52 defining a finger channel therebetween which affords passage of a user's digit to afford removal of the leading end portion 9 of the tape from the land surfaces 34 and 54, and iv) wherein the outer peripheries 15 and 25 are free of any portions extending therebetween other than the tape anchors 30 and 50 to provide an opening for access to the outer peripheral surface 7 of the roll of tape. The method also includes the steps of: B) placing the second side wall 24 substantially opposite the first side wall 14, C) placing the roll of tape 1 between the first and second hub portions 18 and 28; and D) forming a hub which receives the roll of tape 1 by releasably attaching the first hub portion 18 to the second hub portion 28.

Preferably, the step of forming a hub comprises the step of: providing a hub having an axis and an outer hub diameter that is sized and shaped to afford free rotation of the roll of tape about the hub, the hub being adapted to receive the roll of tape 1 in one of either a) a first orientation which affords clockwise rotation of the roll of tape about the axis of the hub, or b) a second orientation which affords counterclockwise rotation of the roll of tape 1 about the axis of the hub.

The present invention has now been described with reference to several embodiments thereof. It will be apparent to those skilled in the art that many insubstantial changes or additions can be made in the embodiments described without departing from the scope of the present invention. Thus, the scope of the present invention should not be limited to the structures described in this application, but only by structures described by the language of the claims and the equivalents of those structures.

What is claimed is:

1. A two-piece protector for a roll of tape having a leading end portion of tape, a pair of sides and edges, a width, an outer peripheral surface defining an outer diameter, and a core defining an inner diameter; said protector comprising:

a first side element comprising a first side wall having an outer periphery with a substantially circular portion defining an outer diameter which is at least as large as the outer diameter of the roll of tape, and a first hub portion;

a second side element comprising a second side wall adapted to be placed substantially opposite said first side wall, said second side wall having an outer periphery having a substantially circular portion defining an outer diameter which is at least as large as the outer diameter of the roll of tape, and a second hub portion;

releasable hub means on said first and second side elements for releasably attaching said first hub portion to said second hub portion to form a hub adapted to receive the roll of tape, said hub having an axis and an outer hub diameter that is sized and shaped to afford free rotation of the roll of tape about the hub, said hub being adapted to receive the roll of tape in one of either a) a first orientation which affords clockwise rotation of the roll of tape about the axis of the hub, or b) a second orientation which affords counterclockwise rotation of the roll of tape about the axis of the hub, said first side element having a first transverse, peripheral tape anchor projecting axially away from said first side wall and toward said second side wall, said first tape anchor having an axially innermost point and a land surface adapted to have a portion of the leading end portion of the tape adhered thereto when the roll of tape is mounted in either the first or the second orientation, said second side element having a second transverse, peripheral tape anchor projecting axially away from said second side wall and toward said first side wall, said second tape anchor having an axially innermost point and a land surface adapted to have a portion of the leading end portion of the tape adhered thereto when the roll of tape is mounted in either the first or the second orientation, the axially innermost points of said first and second tape anchors defining a finger channel therebetween which affords passage of a user's digit to afford removal of the leading end portion of the tape from the land surfaces of said first and second tape anchors, wherein the outer peripheries of said first and second side walls are free of any portions extending therebetween other than said first and second tape anchors to provide an opening for access to the outer peripheral surface of the roll of tape; and wherein the protector is free of any teeth or serrations for cutting the tape.

2. A protector according to claim 1 wherein the outer periphery of said first side wall is substantially the same shape as the outer periphery of the second side wall, and the diameter of the first side wall is approximately equal to the diameter of the second side wall.

3. A protector according to claim 1 wherein said outer hub diameter is less than the inner diameter of the core of the roll of tape to afford free rotation of the roll of tape about said hub.

4. A protector according to claim 1 wherein the first and second elements of said protector are constructed from a plastic material selected from the group consisting of polystyrene, polyethylene, polypropylene and polycarbonate.

5. A protector according to claim 1 wherein said releasable hub means comprises one of said first and second hub portions having a socket portion and the other of said first and second hub portions having a protruding portion adapted to be received in said socket portion in an interference fit.

6. A protector according to claim 5 wherein the protector further includes stabilizing means for restricting rotation of said first side element relative to said second side element.

7. A protector according to claim 6 wherein said stabilizing means comprises one of said first and second hub portions having a key and the other of said first and second hub portions having a slot adapted to receive the key when the releasable hub means forms said hub, said key and slot being situated to resist rotation of said first side element relative to said second side element.

8. A protector according to claim 1 wherein said first and second tape anchors have arcuate edges.

9. A protector according to claim 8 wherein the minimum distance between the axially innermost points of the first and second tape anchors is approximately ⅛ inches.

10. A method of protecting a roll of tape having a leading end portion of tape, a pair of sides and edges, a width, an outer peripheral surface defining an outer diameter, and a core defining an inner diameter; the method comprising the steps of:

A) providing a protector comprising:
  i) a first side element comprising a first side wall having an outer periphery, and a first hub portion; a second side element comprising a second side wall having an outer periphery, and a second hub portion;
  ii) releasable hub means on the first and second side elements for releasably attaching the first hub portion to said second hub portion to form a hub adapted to receive the roll of tape, the hub having an axis and an outer hub diameter that is sized and shaped to afford free rotation of the roll of tape about the hub, the hub being adapted to receive the roll of tape in one of either a) a first orientation which affords clockwise rotation of the roll of tape about the axis of the hub, or b) a second orientation which affords counterclockwise rotation of the roll of tape about the axis of the hub,
  iii) the first side element having a first transverse, peripheral tape anchor projecting axially away from said first side wall and toward said second side wall, said first tape anchor having an axially innermost point and a land surface adapted to have a portion of the leading end portion of the tape adhered thereto when the roll of tape is mounted in either the first or the second orientation, the second side element having a second transverse, peripheral tape anchor projecting axially away from said second side wall and toward said first side wall, said second tape anchor having an axially innermost point and a land surface adapted to have a portion of the leading end portion of the tape adhered thereto when the roll of tape is mounted in either the first or the second orientation, the axially innermost points of said first and second tape anchors defining a finger channel therebetween which affords passage of a user's digit to afford removal of the leading end portion of the tape from the land surfaces of said first and second tape anchors,
  iv) wherein the outer peripheries of said first and second side walls are free of any portions extending therebetween other than said first and second tape anchors to provide an opening for access to the outer peripheral surface of the roll of tape;

B) placing the second side wall substantially opposite the first side wall,

C) placing the roll of tape between the first and second hub portions; and

D) forming a hub which receives the roll of tape by releasably attaching the first hub portion to the second hub portion.

11. A method according to claim 10 wherein the step of forming a hub comprises the step of providing a hub having an axis and an outer hub diameter that is sized and shaped to afford free rotation of the roll of tape about the hub, the hub being adapted to receive the roll of tape in one of either a) a first orientation which affords clockwise rotation of the roll of tape about the axis of the hub, or b) a second orientation which affords counterclockwise rotation of the roll of tape about the axis of the hub.

12. A protector for a roll of hand tearable, medical tape having a leading end portion of tape, a pair of sides and edges, a width, an outer peripheral surface defining an outer diameter, and a core defining an inner diameter; said protector comprising:

a first side element comprising a first side wall having an outer periphery, and a first hub portion;

a second side element comprising a second side wall having an outer periphery, and a second hub portion;

releasable hub means for releasably attaching said first hub portion to said second hub portion to form a hub adapted to receive the roll of tape, said hub having an axis and an outer hub diameter that is sized and shaped to afford free rotation of the roll of tape about the hub, said hub being adapted to receive the roll of tape in one of either a) a first orientation which affords clockwise rotation of the roll of tape about the axis of the hub, or b) a second orientation which affords counterclockwise rotation of the roll of tape about the axis of the hub, said first side element having a first transverse, peripheral tape anchor projecting axially away from said first side wall and toward said second side wall, said first tape anchor having an axially innermost point and a land surface adapted to have a portion of the leading end portion of the tape adhered thereto when the roll of tape is mounted in either the first or the second orientation, said second side element having a second transverse, peripheral tape anchor projecting axially away from said second side wall and toward said first side wall, said second tape anchor having an axially innermost point and a land surface adapted to have a portion of the leading end portion of the tape adhered thereto when the roll of tape is mounted in either the first or the second orientation, the axially innermost points of said first and second tape anchors defining a finger channel therebetween which affords passage of a user's digit to afford removal of the leading end portion of the tape from the land surfaces of said first and second tape anchors, wherein the outer peripheries of said first and second side walls are free of any portions extending therebetween other than said first and second tape anchors to provide an opening for access to the outer peripheral surface of the roll of tape; and wherein the protector is free of any teeth or serrations for cutting the tape.

13. A protector according to claim 12 wherein the outer periphery of the first and second side walls have substantially circular portions defining diameters, and the outer periphery of said first side wall is substantially the same shape as the outer periphery of the second side wall, and the diameter of the first side wall is approximately equal to the diameter of the second side wall.

14. A protector according to claim 12 wherein said outer hub diameter is less than the inner diameter of the core of the roll of tape to afford free rotation of the roll of tape about said hub.

15. A protector according to claim 12 wherein the first and second elements of said protector are constructed from a plastic material selected from the group consisting of polystyrene, polyethylene, polypropylene and polycarbonate.

16. A protector according to claim 12 wherein said releasable hub means comprises one of said first and second hub portions having a socket portion and the other of said first and second hub portions having a protruding portion adapted to be received in said socket portion in an interference fit.

17. A protector according to claim 16 wherein the protector further includes stabilizing means for restricting rotation of said first side element relative to said second side element.

18. A protector according to claim 17 wherein said stabilizing means comprises one of said first and second hub portions having a key and the other of said first and second hub portions having a slot adapted to receive the key when the releasable hub means forms said hub, said key and slot being situated to resist rotation of said first side element relative to said second side element.

19. A protector according to claim 12 wherein said first and second tape anchors have arcuate edges and wherein the minimum distance between the axially innermost points of the first and second tape anchors is approximately ⅜ inches.

* * * * *